United States Patent [19]

Shamshoum et al.

[11] Patent Number: 5,475,180
[45] Date of Patent: Dec. 12, 1995

[54] STABLE TOLUENE DISPROPORTIONATION PROCESS

[76] Inventors: Edwar S. Shamshoum, 14711 Graywood Grove La., Houston, Tex. 77062; Thomas R. Schuler, 400 N. Main, Galena Park, Tex. 77547; Ashim K. Ghosh, 1627 Mabry Mill Rd., Houston, Tex. 77062; James R. Butler, 15718 Crestbrook, Houston, Tex. 77059; James T. Merrill, 2202 Fort Laramie, Katy, Tex. 77449

[21] Appl. No.: 317,511

[22] Filed: Oct. 4, 1994

Related U.S. Application Data

[63] Continuation-in-part of Ser. No. 214,348, Mar. 16, 1994, abandoned, which is a continuation of Ser. No. 663,538, Mar. 4, 1991, abandoned.

[51] Int. Cl.$^6$ .................................................. C07C 5/52
[52] U.S. Cl. ............................................................. 585/475
[58] Field of Search ................................................ 585/475

[56] References Cited

U.S. PATENT DOCUMENTS

| | | | |
|---|---|---|---|
| 3,957,621 | 5/1976 | Bonacci et al. | 208/60 |
| 4,078,990 | 3/1978 | Brennan et al. | 208/64 |
| 4,150,061 | 4/1979 | Feinstein et al. | 585/475 |
| 4,211,886 | 7/1980 | Tabak et al. | 585/321 |
| 4,341,622 | 7/1982 | Tabak et al. | 208/66 |

*Primary Examiner*—P. Achutamurthy

[57] ABSTRACT

A process is provided for the disproportionation of a toluene feedstock over a metal promoted mordenite catalyst. The catalyst may contain between 1.0–1.5 weight percent nickel. The toluene feedstock is supplied to the reaction zone and into contact with the catalyst. The reaction zone is operated under disproportionation conditions. During disproportionation, heavy aromatic reformates, in concentration of at least 4 weight percent, are introduced into the reaction zone. Disproportionation product containing benzene and xylene is continuously withdrawn. The addition of the heavy aromatic reformate does not adversely affect toluene conversion rates, product selectivity to benzene, catalyst activity or catalyst life. Moreover, production of xylenes increase at the expense of production of heavies.

13 Claims, 3 Drawing Sheets

STABLE TOLUENE DISPROPORTIONATION PROCESS

This is a continuation-in-part of application Ser. No. 08/214,348 filed Mar. 16, 1994, abandoned, which was a continuation of application Ser. No. 07/663,538 filed Mar. 4, 1991, abandoned.

FIELD OF THE INVENTION

This invention relates to the disproportionation of alkylaromatic feedstreams and more particularly to the disproportionation of toluene containing feedstocks employing mordenite catalysts.

DESCRIPTION OF THE RELATED ART

The disproportionation of toluene involves a well known transalkylation reaction in which toluene is converted to benzene and xylene in accordance with the following reaction:

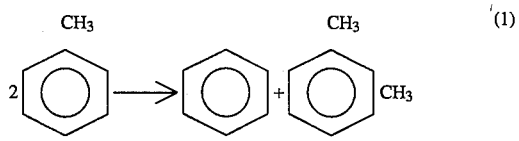

Reaction (1) is mildly exothermic.

Mordenite is one of a number of molecular sieve catalysts useful in the transalkylation of alkylaromatic compounds. Mordenite is a crystalline aluminosilicate zeolite exhibiting a network of silicon and aluminum atoms interlinked by oxygen atoms within the crystalline structure. For a general description of mordenite catalysts, reference is made to Kirk-Othmer, *Encyclopedia of Chemical Technology*, 3rd Edition, 1981, under the heading "Molecular Sieves", Vol. 15, pages 638–643. Mordenite as found in nature or as synthesized to replicate the naturally occurring zeolite, typically exhibits a relatively low silica to alumina mole ratio of about 10 or less. Also known, however, are mordenite catalysts exhibiting a substantially lower alumina content. These aluminum deficient mordenite catalysts exhibit silica to alumina ratios greater than 10, ranging up to about 100, and may be prepared by direct synthesis as disclosed, for example, in U.S. Pat. No. 3,436,174 to Sand or by acid extraction of a more conventionally prepared mordenite as disclosed in U.S. Pat. No. 3,480,539 to Voorhies. Both the typical and the aluminum deficient mordenites are known to be useful in the disproportionation of toluene.

General operating conditions relating to the disproportionation of toluene feedstock include temperatures ranging from about 200° C. to about 600° C. or above and pressures ranging from atmospheric to perhaps 100 atmospheres or above. The specific catalyst, however, may impose constraints on reaction temperatures in terms of catalyst activity and aging characteristics. In general, the prior art suggests the use of relatively high temperatures when employing the high aluminum mordenites (low silica to alumina ratios) and somewhat lower temperatures when employing the low alumina mordenites. Accordingly, where mordenite catalysts exhibiting high silica to alumina ratios have been employed in the transalkylation of alkylaromatics, it has been the practice to operate toward the lower end of the temperature range.

U.S. Pat. No. 4,665,258 to Butler, however, discloses a toluene disproportionation process employing an aluminum deficient mordenite catalyst, involving a temperature range of 370°–500° C. The mordenite catalysts described therein exhibit silica/alumina mole ratios of at least 30 and, more desirably, within the range of 40–60. The toluene weight hourly space velocity (WHSV) may be greater than 1. Hydrogen is supplied to the reaction zone at a hydrogen/toluene mole ratio within the range of 3–6, at a pressure of 500 psi or more.

Butler '258 also discloses passing a hot preflush gas, nitrogen or hydrogen, to the reaction zone prior to initiating the disproportionation reaction. The preflush gas is heated to a temperature sufficient to substantially dehydrate the catalyst by the time the toluene feed is started. This measure enables the disproportionation process to initially be performed at a somewhat lower temperature and without reduction in toluene conversion. As the disproportionation proceeds, temperature progressively increases to maintain toluene conversion at the desired level, typically about 80 percent of theoretical.

U.S. Pat. No. 4,723,049 to Menard discloses toluene disproportionation carried out over aluminum deficient mordenite of the type disclosed in the aforementioned patent to Butler, with a reaction zone temperature of 370°–500° C. Menard '049 employs an interruption procedure whereby the supply of toluene to the reaction zone is interrupted while the supply of hydrogen is continued. This mode of operation is disclosed to enhance the aging quality of the catalyst and show a reduction in reactor zone temperature without a corresponding decrease in toluene conversion.

It is also a common practice to promote an aluminum deficient mordenite catalyst with a catalytically active metallic content. For example, U.S. Pat. No. 3,476,821 to Brandenburg discloses disproportionation reactions employing mordenite catalysts having silica/alumina ratios within the range of 10–100 and preferably within the range of about 20–60. The mordenites are modified by the inclusion of a sulfided metal selected from the Group VIII metals. The especially preferred sulfided Group VIII metals are cobalt and nickel present in a concentration of 0.5–10 weight percent. Brandenburg '821 discloses temperature ranges from about 400°–750° F. The metal promoters are said to substantially increase activity and catalyst life, as indicated by runs extending over several hours or days.

As noted previously, hydrogen is commonly supplied along with toluene to the reaction zone. While the disproportionation reaction (1) does not involve chemical consumption of hydrogen, the use of a hydrogen co-feed is generally considered to prolong the useful life of the catalyst, as disclosed, for example, in the above mentioned patent to Brandenburg '821. The amount of hydrogen supplied, which is normally measured in terms of the hydrogen/toluene mole ratio, is generally shown in the prior art to increase as temperature increases.

Bhavikatti, "Toluene Disproportionation Over Aluminum-Deficient and Metal-Loaded Mordenites. 1. Catalytic Activity and Aging", Ind. Eng. Chem. Prod. Res. Dev. 1981, 20, 102–105, discloses toluene disproportionation at 400° C. over mordenite catalysts having silica/alumina mole ratios ranging from 12 to 61 at atmospheric pressure and a space velocity (WHSV) of 1. Bhavikatti indicates that an increase in the silica/alumina mole ratio decreases catalyst activity, while aging quality is increased (i.e., lowering aging rates). Catalyst decay was also suppressed by loading the mordenites with nickel.

U.S. Pat. No. 3,562,345 to Mitsche discloses the use of molecular sieves such as mordenite catalysts in the disproportionation of toluene. The catalysts are characterized by a silica/alumina mole ratio from about 6 to about 12, pore openings of from about 3 to about 18 angstroms and the incorporation of catalytically active metallic materials in the oxidized or reduced state, particularly Group VIB and Group VIII metals including molybdenum, tungsten, chromium, iron, nickel, cobalt, platinum, palladium, ruthenium, rhodium, osmium, and iridium. Mitsche '345 discloses transalkylation at temperatures from about 200° C. to about 480° C. and gives specific examples of transalkylation of toluene at temperatures of 420° C. and 450° C.

U.S. Pat. No. 3,677,973 to Mitsche, discloses the use of mordenite catalysts composited with an alumina salt providing a silica/alumina mole ratio of about 10 to about 30 in the disproportionation of toluene. The reaction conditions proposed in Mitsche '973 appear similar to those set forth in the aforementioned Mitsche '845 patent and, like the former patent, Mitsche '973, discloses incorporating Group VIB and Group VIII metals into the catalyst.

U.S. Pat. No. 4,151,120 to Marcilly discloses a process for the manufacture of a hydrocarbon conversion catalyst involving incorporating cobalt, nickel, silver or palladium in a mordenite catalyst having a silica/alumina mole ratio within the range of 10-100. Following incorporation of the metal into the mordenite, the catalyst is dried and subjected to a dry calcination procedure at a temperature within the range of 300°–700° C. in the presence of an inert or oxidizing gas having a moisture content of less than 1 percent. Marcilly '120 discloses various examples of the dismutation of toluene under reaction conditions 420° C., 30 bars, a space velocity (WHSV) of 5 and a hydrogen/ hydrocarbon mole ratio of 5.

U.S. Pat. No. 4,723,048 to Dufresne discloses a process for the dismutation of toluene employing a zeolite catalyst modified by the inclusion of metals. The catalyst is described as a sodium containing mordenite in the nature of so-called "wide pore" mordenite, i.e., mordenite with main pores exhibiting a diameter of 7–10 Angstroms or "small pore" mordenite, mordenites with main pores exhibiting a diameter of 4–6 Angstroms. The mordenites are treated to extract sodium therefrom to provide not more than 1 percent by weight sodium ions and preferably not more than 0.5 percent by weight sodium ions.

An important and distinguishing feature of the present invention is that no specialized, pre-reaction start-up procedure is required. As indicated in the foregoing discussion, however, the prior art encompasses a variety of such techniques.

For example, passing a hot, inert gas (hydrogen or nitrogen) across the catalyst and reactor bed prior to feedstock introduction is disclosed in U.S. Pat. No. 4,956,511 to Butler and Butler '258. Another pre-reaction, start-up procedure aimed at controlling the hygroscopic tendency of mordenite involves subjecting the catalyst to a dry calcination procedure as disclosed in U.S. Pat. No. 4,151,120 to Marcilly. A related pre-reaction, start-up procedure which, additionally, is not required in the present invention involves dehydration of the toluene feedstock as disclosed by Pollitzer, U.S. Pat. No. 3,780,122. As explained therein, even a very small amount of water (15 ppm) reduces toluene conversion substantially. Accordingly, the patent designates an upper limit of 25 ppm water in the feedstock. None of the references teach or suggest the disproportionation of toluene feedstocks containing heavy aromatic reformates comprising trimethylbenzenes and ethyltoluenes. Because one of the side reactions taking place in toluene disproportionation produces heavy aromatic reformates, which have a lower economic value than toluene, a long felt need exists for an improved procedure for use in disproportionation that would increase the production of higher valued products such as xylene or benzene at the expense of the production of such heavy aromatic reformate without reducing catalyst life.

SUMMARY OF THE INVENTION

In accordance with the present invention, there is provided a process for the disproportionation of a pure toluene feedstock over a metal promoted mordenite catalyst and the introduction of heavy aromatic reformate without adversely affecting catalyst activity and aging quality. One aspect of the conventional toluene disproportionation process is the production of heavy aromatic reformates. The inventors have found that recycling these heavy aromatic reformates (i.e., introducing same with the toluene feedstock) increases product selectivity to xylene at the expense of the production of heavy aromatic reformates. In practicing the invention, a toluene feedstock is supplied to a reaction zone containing a metal promoted mordenite catalyst. Hydrogen is also supplied to the reaction zone to provide a hydrogen environment. Heavy aromatic reformates comprising mostly xylenes, ethyltoluenes and trimethylbenzenes are introduced to the reaction zone in amounts of at least four weight percent. The reaction zone is operated under temperature and pressure conditions to effect the disproportionation of toluene to benzene and xylene. The disproportionation product containing these compounds is withdrawn from the reaction zone. Preferably the reaction zone is operated at a temperature within the range of about 300°–500° C. and a pressure of at least 550 psig.

BRIEF DESCRIPTION OF THE DRAWING

Further aspects of the invention and their advantages may be discerned when one refers to the following detailed description as taken in conjunction with the drawings in which.

DESCRIPTION OF THE PREFERRED EMBODIMENTS

Figure 1:
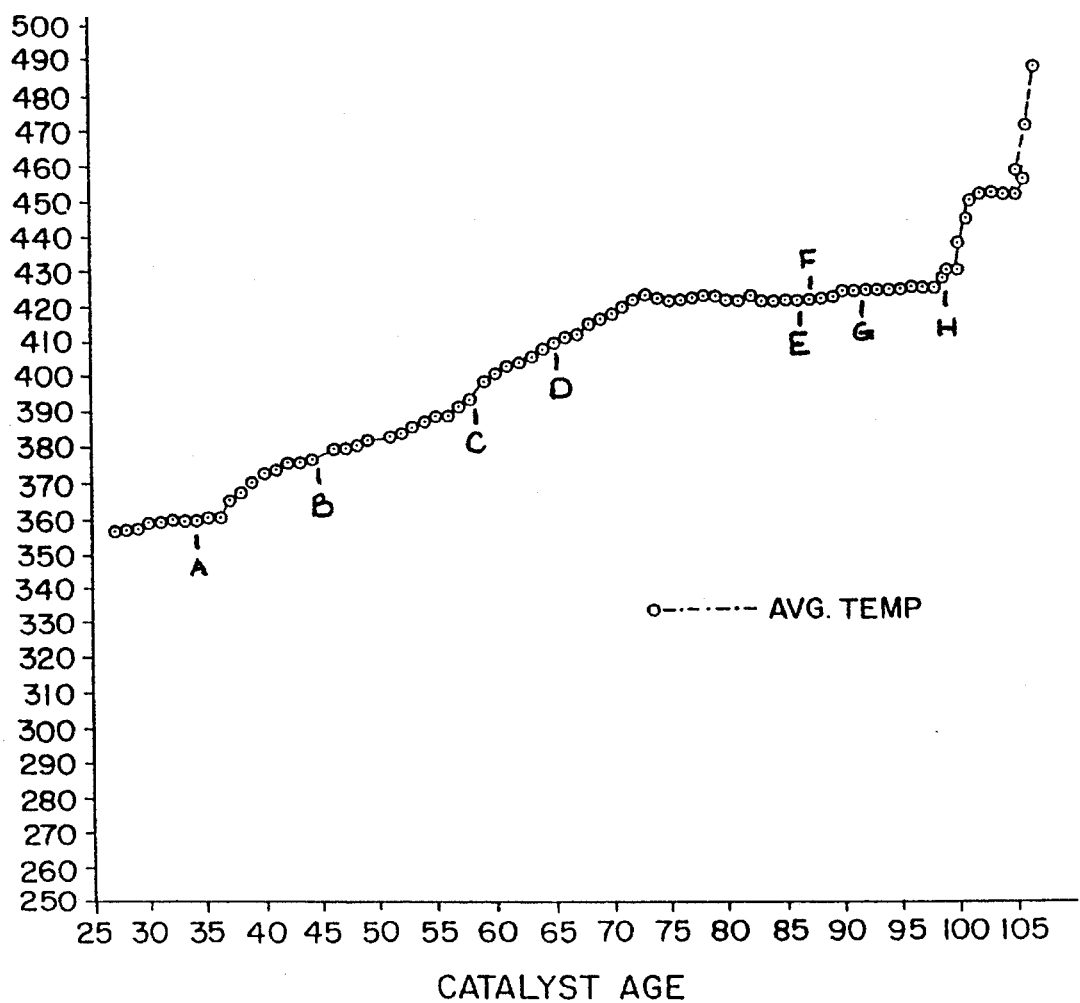
FIG. 1 is a graph illustrating stable toluene conversion in a disproportionation process carried out over a nickel modified mordenite catalyst wherein the toluene feedstock contains up to 12.5 weight percent heavy aromatic reformate.

The present invention relates to a toluene disproportionation process. As is well known in the art, one product of the toluene disproportionation process is the production of heavy aromatic reformate ("heavies"), including ethyltoluenes and trimethylbenzenes. Currently these heavies are blended into gasoline, which has the net affect of converting toluene into a gasoline blend stock. For current economic reasons, it is preferable to lower the size of this stream to the gasoline pool. In the present invention, heavies are recycled through the toluene disproportionation process, thereby reducing the size of the heavies stream to the gasoline pool.

This recycling also increases the product selectivity to xylenes. Further, the present invention provides a process for the disproportionation of a combination of substantially pure toluene feedstock and the introduction of heavy aromatic reformate over a mordenite catalyst without affecting catalyst activity and aging quality. The preferred catalyst comprises a metal promoted mordenite catalyst.

In accordance with the invention, the toluene disproportionation process begins with supplying a substantially pure toluene feedstock to a reaction zone containing a metal promoted mordenite catalyst. The reaction zone is operated under disproportionation conditions including a temperature within the range of 250° C. to 500° C. and a pressure of at least 550 psig. Contemporaneous with the toluene, hydrogen gas is cored to the reaction zone to provide a hydrogen environment. The feedstock contacts the catalyst forming a disproportionation product containing benzene, xylene(s) and nonaromatic by-products, along with heavy aromatic reformate. The heavy aromatic reformate includes the xylene and heavier cut from a naptha reformer or the trimethylbenzene and heavier by-products from toluene disproportionation. The heavy aromatic reformate, which would include ethyltoluenes and trimethylbenzene is then recycled to pass through the reaction zone simultaneously with the toluene and hydrogen. Disproportionation product is continuously withdrawn as the process continues.

The mordenite catalyst employed in the present invention is modified by the inclusion of a metallic hydrogenation component, more specifically nickel, in which catalyst activity and aging quality are enhanced to yield toluene conversion rates of at least 48 percent at relatively low temperature and rate of catalytic deactivation. The mordenite catalyst employed in the present invention preferably exhibits, but is not limited to, a silica to alumina mole ratio of between 16:1 to 29:1. Applicant's experimentation suggests that best results are obtained by utilizing a catalyst made up of no less than 1.0 weight percent nickel. It is known that low nickel content mordenite catalysts provide toluene conversion and selectivity to xylenes and benzene but exhibit poor aging qualities. Experimentation has determined that greater amounts of nickel can be used, however, examples herein used a nickel content in the catalyst is about 1.0–1.5 weight percent.

Figure 2:
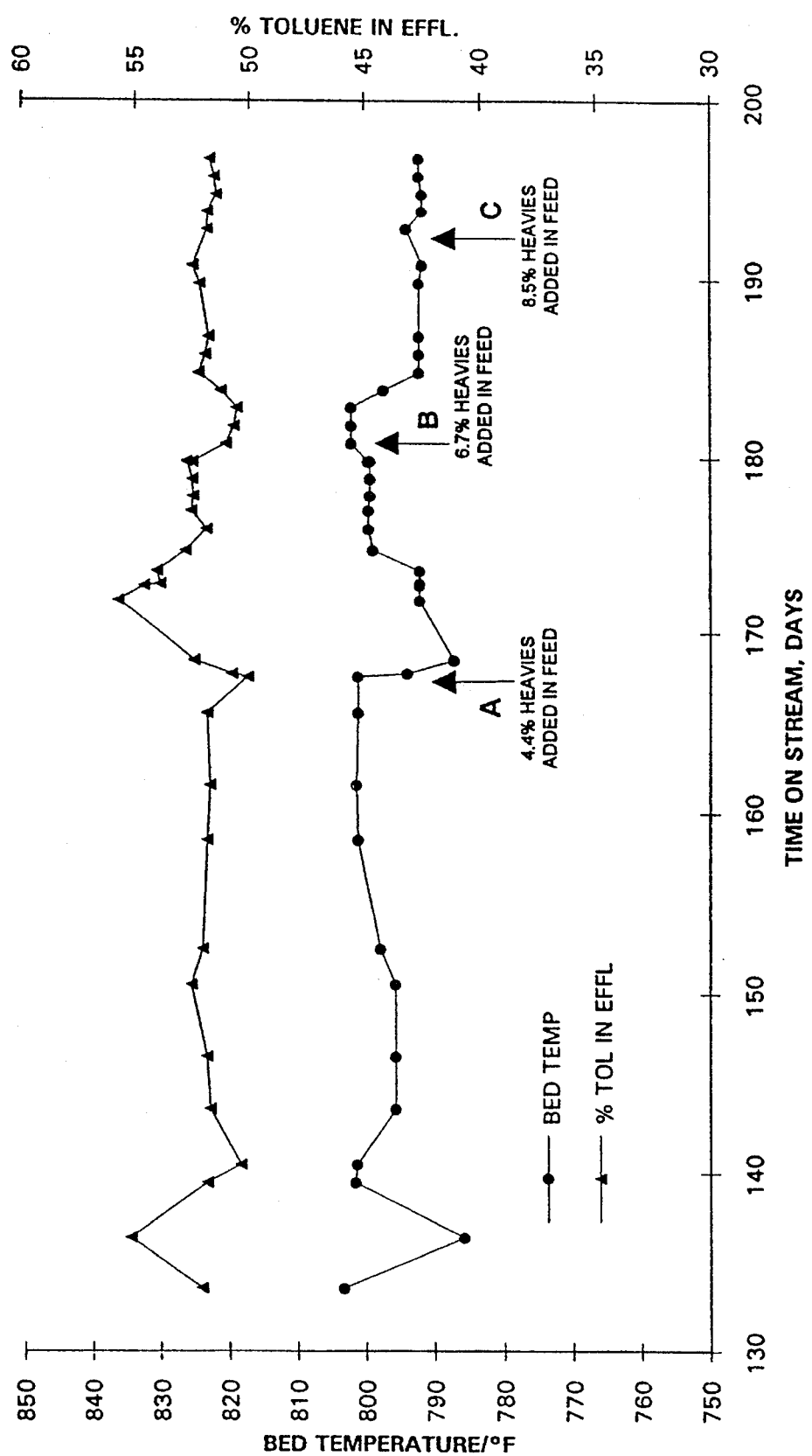
FIG. 2 is a graph illustrating toluene concentration in the effluent, i.e., product selectivity to toluene, as a function of catalyst age and the addition of heavy aromatic reformate in weight percentage amounts of 4.4, 6.7 and 8.5 percent.
Figure 3:
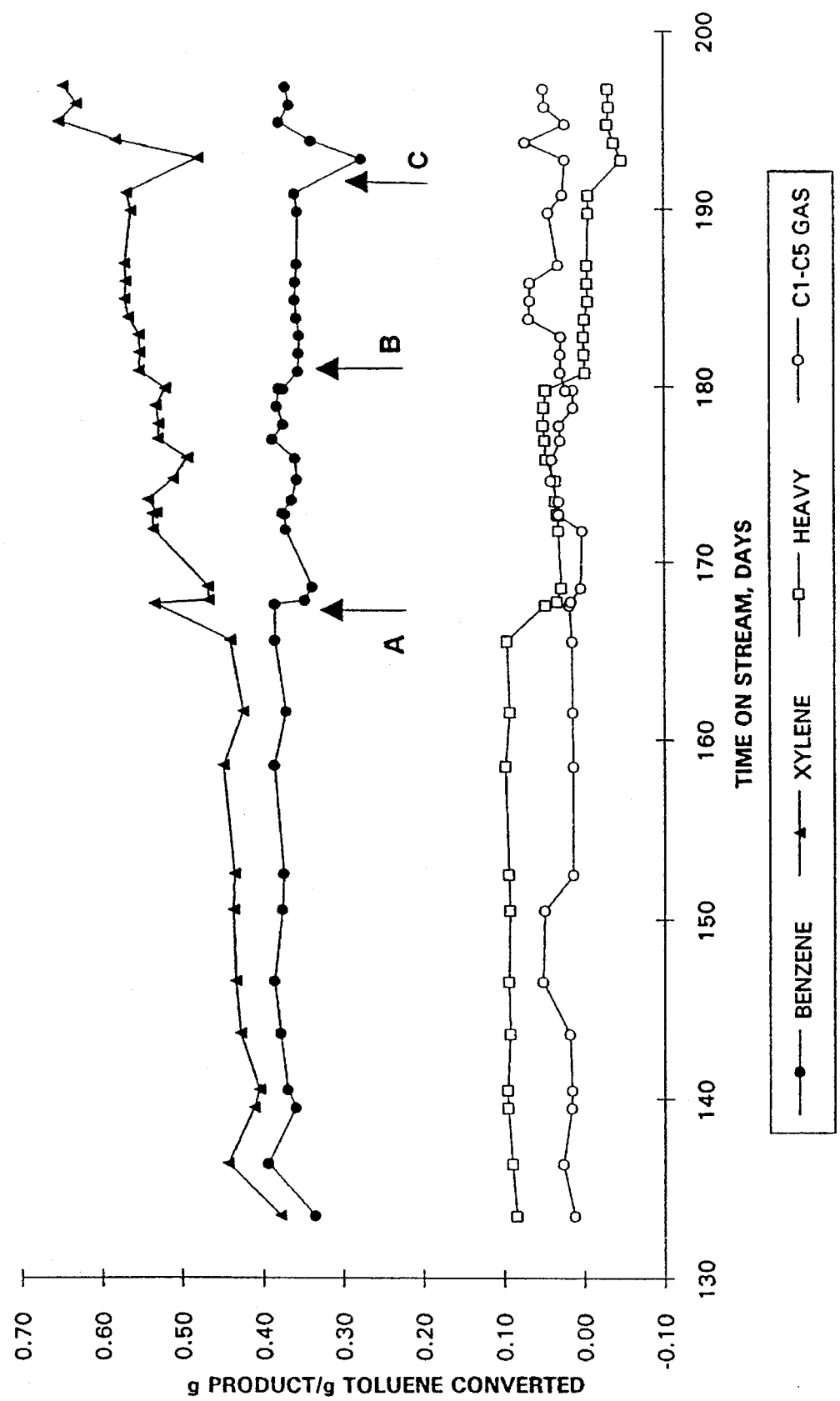
FIG. 3 is a graph illustrating the number of grams of each of the following products, benzene, xylene, heavies and $C_1$–$C_5$ gases per gram of toluene convened, where pure toluene feedstock is used and where heavy aromatic reformate is added in weight percentage amounts of 4.4, 6.7 and 8.5 percent.

The present invention resulted from studies conducted over a period of at least 100 days utilizing a laboratory reactor. FIGS. 1–3 graphically characterize the distinct advantages of the present invention in conjunction with the following Examples 1–2. The figures are further described hereinbelow as the following examples are discussed.

EXAMPLE 1

Example 1 resulted from a study conducted over a period of 107 days using a laboratory reactor. In the presence of hydrogen gas, a substantially pure toluene feedstock was supplied to a reaction zone containing a nickel promoted mordenite catalyst under temperature and pressure conditions within the range of 300°–500° C. and at least 550 psig, respectively, with the mordenite catalyst having a nickel content of about 1.4 weight percent. Hydrogen was supplied to the reaction zone in an amount to provide a hydrogen/toluene mole ratio of about 3 to 4 and the feedstock weight hourly space velocity (WHSV) was between about 2.0–2.7.

Heavy aromatic reformate was introduced to the reaction zone without adversely affecting toluene conversion levels. The heavy aromatic reformate utilized constituted refinery by-product and, upon analysis, was determined to consist principally of the following: 37.6 percent xylenes (mainly ortho-xylene=24.01%), 23.2 percent ethyltoluenes (ET) (mostly meta-ET=19.97%) and 24.3 percent trimethylbenzenes (TMB) (mostly 1, 2, 4 TMB=15.16%). FIG. 1 graphically depicts reaction bed temperature versus catalyst age as toluene conversion rates are maintained at a level of at least 48 weight percent, and heavy aromatic reformate is introduced to the reaction zone as indicated on FIG. 1.

During the first part of the reactor run, toluene feed was mixed alternately with 5 percent, 7.5 percent and 12.5 percent of heavy aromatic reformate starting on days 34, 45, and 58, respectively. (See FIG. 1, points A, B and C, respectively.) In all cases, normalized toluene conversion [(toluene (in)–toluene (out))/toluene (in)×100] dropped soon after the addition of the reformate or after the increase in its concentration. As a result, the temperature was increased to maintain a base level of 48 percent toluene conversion. For each of the three introductions of aromatic reformate, catalyst deactivation rates were measured at 1.5° C./day, 0.94° C./day and 2.5° C./day, respectively.

During the second part of the reactor run, toluene feed was introduced in a substantially pure form starting on day 65 and ending on day 86. (See FIG. 1, points D and E, respectively.) Toluene conversion increased from 48 percent on day 65 to 53 percent on day 72. As a result, the temperature was increased from 412° C. to 423° C. with a corresponding average catalyst deactivation rate of 1.38° C./day. Beginning on day 73, the average reactor bed temperature (automatically) stabilized between 420° C.–425° C. for a period of 27 days even though toluene conversion had risen and was being maintained at a level of between 53 percent–54 percent.

Finally, beginning on day 87 (See FIG. 1, point F) and continuing through day 91, and beginning on day 92 (See FIG. 1, point G) and continuing through 98, 7.5 and 12.5 weight percent heavy aromatic reformate, respectively, was cofed with the toluene, which, importantly, did not disturb the catalyst stability or high level of conversion that had been attained. Accordingly, a distinct advantage of the present invention is graphically illustrated in FIG. 1, which indicates that, by utilizing the catalyst of the present invention, a successful toluene conversion level in excess of 50 percent with negligible catalytic deactivation was achieved at a relatively low temperature of approximately 420° C. This advantage was recognized even under the relatively harsh conditions wherein the feedstock contained between 7.5 and to 12.5 percent by weight heavy aromatic reformate. On day 99, a 25 weight percent concentration of aromatic reformate was purposely cored with the toluene to determine catalyst tolerance toward higher levels of conversion. (See FIG. 1, point H.)

The following table describes the percent toluene conversion rates achieved during days 87 through 108 when heavy aromatic reformates were introduced at weight percent levels of 7.5, 12.5 and 25.

TABLE 1

Introduction of Heavy Aromatic Reformate to Toluene Feedstock and Effect on Toluene Conversion

|  | Day | % Toluene Conversion |
|---|---|---|
| Introduction of 7.5% Heavies | 87 | 51.99 |
|  | 88 | 52.18 |
|  | 89 | 54.46 |
|  | 90 | 52.57 |
|  | 91 | 54.98 |
| Introduction of 12.5% Heavies | 92 | 54.49 |
|  | 93 | 52.61 |
|  | 94 | 50.58 |
|  | 95 | 50.37 |

TABLE 1-continued

Introduction of Heavy Aromatic Reformate to Toluene Feedstock and Effect on Toluene Conversion

| | Day | % Toluene Conversion |
|---|---|---|
| | 96 | 50.62 |
| | 97 | 50.82 |
| | 98 | 50.60 |
| Introduction of 25% Heavies | 99 | 50.53 |
| | 100 | 46.93 |
| | 101 | 50.04 |
| | 102 | 50.77 |
| | 103 | 50.84 |
| | 104 | 50.66 |
| | 105 | 52.31 |
| | 106 | 61.48 |
| | 107 | 63.46 |

While the inventors believe both that the stable reaction conditions achieved during days 73–100 could have been maintained indefinitely, and that greater than 12.5 weight percent aromatic reformate can be added to the toluene feedstock without disrupting same, they were unable to document this because an unexpected drop in reactor pressure occurred, causing the termination of the reactor run.

EXAMPLE 2

Example 2 resulted from a study conducted over a period of 200 days using a laboratory reactor. In the presence of hydrogen gas, a substantially pure toluene feedstock was supplied to a reaction zone containing a nickel promoted mordenite catalyst under the following initial conditions: temperature and pressure conditions within the range of 300°–500° C. and at least 550 psig, respectively; nickel content in the catalyst of about 1.1 weight percent; hydrogen/toluene mole ratio of about 3 to 4; and liquid hourly space velocity (LHSV) of about 2.0. In this Example 2, approximately 4 to 9% of heavy aromatic reformate consisting predominately of trimethylbenzenes (TMB) was added to the toluene feed at the conditions as described above. (See FIG. 2.) Production of xylenes increased significantly at the expense of heavy aromatics (see FIG. 3) while the production of benzenes decreased insignificantly.

FIG. 2 graphically illustrates the effect on toluene conversion levels of the introduction of heavy aromatic reformate to the reaction zone. From day 1 through day 166, pure toluene feedstock was supplied to the reaction zone as described above. During this period, the catalyst was stabilized. Beginning on day 167 (Jul. 15, 1993), pure toluene feed was replaced by the following feed: nonaromatics 0.049, toluene 95.614, EB 0.012, p-xylene 0.011, m-xylene 0.019, o-xylene 0.003, p-ethyltoluene 0.185, m-ethyltoluene 0.174, o-oethyltoluene 0.155, 1,3,5-TMB 0.931, 1,2,4-TMB 2.443, 1,2,3-TMB 0.358, other heavies 0.037 and unknown 0.009 weight percent (xylenes, ethyltoluenes and TMB comprising 4.3 weight percent, total heavies approximately 4.4 weight percent). (See FIG. 2, point A.)

On day 180 (July. 31, 1993), feed composition was changed to: nonaromatics 0.045, toluene 93.345, EB 0.010, p-xylene 0.010, m-xylene 0.019, o-xylene 0.003, p-ethyltoluene 0.101, m-ethyltoluene 0.010, o-ethyltoluene 0.098, 1.3.5-TMB 1.428, 1,2,4-TMB 4.226, 1,2,3-TMB 0.627, other heavies 0.059 and unknown 0.019 weight percent (xylenes, ethyltoluenes and TMB comprising approximately 6.5 weight percent, total heavies approximately 6.7 weight percent). (See FIG. 2, point B.)

On day 192 (Aug. 11, 1993), feed composition was changed to: nonaromatics 0.048, benzene 0.002, toluene 91.493, EB 0.009, p-xylene 0.009, m-xylene 0.019, o-xylene 0.004, m-ethyltoluene 0.014, o-ethyltoluene 0.021, 1,3,5-TMB 4.063, 1,2,4-TMB 2.378, 1,2,3-TMB 1.740, m-DEB 0.004, other heavies 0.168 and unknown 0.028 weight percent (xylenes, ethyltoluenes and trimethylbenzenes comprising approximately 8.2 weight percent, total heavies approximately 8.5 weight percent). (See FIG. 2, point C.)

As described, 4.4–8.5 wt % heavies, predominantly trimethylbenzenes (TMB), were added to the toluene feed at conditions where the catalyst had shown very little deactivation. The toluene concentration in product effluent was maintained at 52 weight percent irrespective of the amount of heavies added in the feed. FIG. 2 shows that adding 4.4 weight percent heavies on day 167,(Jul. 15, 1993) (FIG. 2, point A), 6.7 weight percent heavies on day 180 (Jul. 31, 1993) (FIG. 2, point B), or 8.5 weight percent heavies on day 192 (Aug. 11, 1993) (FIG. 2, point C) did not require any increase in catalyst bed temperature to maintain a constant toluene concentration in the effluent. In fact the temperature was decreased by about 8° F. to maintain toluene concentration at 52 weight percent in the product effluent. The results suggest that the addition of heavies in toluene feed causes no catalyst deactivation after catalyst stabilization.

FIG. 3 graphically depicts the number of grams of benzene, xylene, heavies and $C_1$–$C_5$ gases produced for each gram of toluene converted in the instant process. Points A, B and C illustrate the points at which 4.4, 6.7 and 8.5 weight percent heavy aromatic reformate was introduced to the feed composition. The production of benzene was found to be 0.38 gram per gram of toluene converted when pure toluene feed was used. The production of benzene decreased slightly when heavy aromatics were added in the feed (see FIG. 3). The formation of xylenes increased significantly at the expense of heavies which can be explained by the reverse disproportionation of xylenes:

$$\text{Toluene} + \text{TMB} \rightarrow 2 \text{ Xylene}$$

There was a slight increase in nonaromatic C1–C5 gases perhaps due to the dealkylation of some heavy aromatics.

In summary, recycling heavy aromatic reformates during toluene disproportionation does not adversely affect toluene conversion rates, nor markedly decrease product selectivity to benzene. In addition, catalyst activity or catalyst life is not markedly adversely affected. Moreover, product selectivity to xylene is increased at the expense of the production of heavies.

While the invention has been described with reference to particular embodiments thereof, it will be apparent to those skilled in the art that various changes and modifications can be made without departing from the spirit of the invention or from the scope of the appended claims.

We claim:

1. A transalkylation process for the disproportionation of a toluene containing feedstock over a metal promoted mordenite catalyst to produce benzene and xylene, the steps comprising:

(a) establishing a reaction zone by loading into said reaction zone a nickel modified mordenite catalyst, said reaction zone operated under disproportionation conditions;

(b) passing said toluene containing feedstock into said reaction zone and into contact with said catalyst;

(c) introducing into said reaction zone and into contact with said catalyst at least 4 percentage concentration by weight of a heavy aromatic reformate consisting mostly of xylenes, ethyltoluenes and trimethylbenzenes; and (d) withdrawing said disproportionation product containing benzene and xylene from said reaction zone.

2. The process according to claim 1, wherein said reaction zone is operated at a temperature within the range of 300°–500° C. and at a pressure of at least 550 psig.

3. The process according to claim 1, wherein said reaction zone is operated at a temperature within the range of 400°–450° C.

4. The process according to claim 1, wherein said mordenite catalyst has a silica to alumina molar ratio of about 16:1 to 29:1.

5. The process according to claim 1, wherein said mordenite catalyst contains an amount of nickel within the range 1.0–1.5 weight percent.

6. The process accordingly to claim 1, wherein said heavy aromatic reformate is introduced into said reaction zone at an amount between about 4 weight percent concentration by weight and about 12.5 percentage concentration by weight.

7. The process accordingly to claim 1, wherein said heavy aromatic reformate is introduced into said reaction zone at an amount between about 4 weight percent concentration by weight and about 8.5 percentage concentration by weight.

8. A transalkylation process for the disproportionation of a toluene containing feedstock over a metal promoted mordenite catalyst to produce benzene and xylene, the steps comprising:

(a) passing a cofeed of substantially pure toluene feedstock and about 7 percentage concentration by weight of a heavy reformate consisting mostly of xylenes, ethyltoluenes and trimethylbenzenes into a reaction zone and contacting it with a mordenite catalyst modified by the inclusion of nickel within the reaction zone, said feedstock being supplied to said reaction zone at a rate sufficient to provide a toluene WHSV greater than about 1;

(b) conducting the disproportionation reaction within said reaction zone at a temperature within the range of 350°–450° C. and a pressure of at least 550 psig; and (c) withdrawing said disproportionation product containing benzene and xylene from said reaction zone.

9. The process accordingly to claim 8, wherein said mordenite catalyst has a silica to alumina molar ratio of about 16:1 to 29:1.

10. The process according to claim 8, wherein said metal promoted mordenite catalyst contains an amount of nickel within the range 1.0–1.5 weight percent.

11. A transalkylation process for the disproportionation of a toluene containing feedstock over a metal promoted mordenite catalyst to produce benzene and xylene, the steps comprising:

(a) passing a cofeed of substantially pure toluene feedstock and about 7 up to about 12.5 percentage concentration by weight of a heavy reformate consisting mostly of xylene(s), ethyltoluenes and trimethylbenzenes into a reaction zone and contacting it with a mordenite catalyst modified by the inclusion of nickel within the reaction zone, said feedstock being supplied to said reaction zone at a rate sufficient to provide a toluene weight hourly space velocity (WHSV) greater than about 1;

(b) conducting the disproportionation reaction within said reaction zone at a temperature within the range of 350° to 450° C. and at a pressure of at least 550 psig; and (c) withdrawing said disproportionation product containing benzene and xylene(s) from said reaction zone.

12. The process accordingly to claim 11, wherein said mordenite catalyst has a silica to alumina molar ratio of about 16:1 to 29:1.

13. The process according to claim 11, wherein said metal promoted mordenite catalyst contains an amount of nickel within the range 1.0–1.5 weight percent.

* * * * *